United States Patent
Hasse et al.

(10) Patent No.: US 7,112,192 B2
(45) Date of Patent: Sep. 26, 2006

(54) TAMPON WITH AN OVERWRAP OR OVERWRAPS HAVING BOTH MASKING AND WICKING PROPERTIES

(75) Inventors: Margaret Henderson Hasse, Wyoming, OH (US); Steven Ray Gilbert, Fairfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 459 days.

(21) Appl. No.: 10/298,403

(22) Filed: Nov. 18, 2002

(65) Prior Publication Data

US 2003/0097106 A1 May 22, 2003

Related U.S. Application Data

(63) Continuation-in-part of application No. 09/993,988, filed on Nov. 16, 2001, now Pat. No. 6,840,927.

(51) Int. Cl.
A61F 13/15 (2006.01)
A61F 13/20 (2006.01)

(52) U.S. Cl. .................... 604/385.17; 604/904
(58) Field of Classification Search ......... 604/385.17, 604/385.18, 363, 904
See application file for complete search history.

(56) References Cited

U.S. PATENT DOCUMENTS

| | | | |
|---|---|---|---|
| 2,264,586 A * | 12/1941 | Ross | 604/15 |
| 2,601,633 A | 5/1952 | Riordan | |
| 3,135,262 A * | 6/1964 | Kobler et. al. | 604/385.18 |
| 3,732,866 A | 5/1973 | Accavallo | |
| 4,027,673 A | 6/1977 | Poncy | |
| 4,041,948 A * | 8/1977 | Flam et al. | 604/369 |
| 4,215,683 A * | 8/1980 | Lundin et al. | 128/864 |
| 4,338,929 A * | 7/1982 | Lundin et al. | 128/864 |
| 4,498,469 A * | 2/1985 | Csiki | 128/867 |
| 4,661,101 A * | 4/1987 | Sustmann | 604/360 |
| 5,891,123 A | 4/1999 | Balzar | |
| 6,177,608 B1 | 1/2001 | Weinstrauch | |
| 6,186,995 B1 | 2/2001 | Tharpe, Jr. | |
| 6,258,075 B1 | 7/2001 | Taylor | |
| 2002/0142693 A1 | 10/2002 | Buzot | |
| 2002/0156343 A1 | 10/2002 | Zunker | |
| 2003/0093049 A1* | 5/2003 | Johnson et al. | 604/370 |

FOREIGN PATENT DOCUMENTS

| | | |
|---|---|---|
| GB | 2 227 666 A | 8/1990 |
| JP | 08-117282 | 5/1996 |
| WO | WO 02/078587 A1 | 10/2002 |

* cited by examiner

Primary Examiner—Michele Kidwell
(74) Attorney, Agent, or Firm—James E. Oehlenschlager; Bridget S. Ammons; David M. Weirich

(57) ABSTRACT

An improved absorbent catamenial tampon is disclosed comprising an overwrap with both a masking region and a wicking region. The compressed absorbent member of the tampon has an inner region, an exterior surface, and an insertion end opposed to a withdrawal end. The overwrap comprises a masking region and a wicking region. The wicking region of the overwrap covers at least a portion of the exterior surface of the compressed absorbent member proximal to the withdrawal end of the compressed absorbent member. The masking region surrounds at least a portion of the exterior surface of the compressed absorbent member proximal to the insertion end of the compressed absorbent member.

8 Claims, 3 Drawing Sheets

TAMPON WITH AN OVERWRAP OR OVERWRAPS HAVING BOTH MASKING AND WICKING PROPERTIES

CROSS REFERENCE TO RELATED APPLICATIONS

This is continuation-in-part of the co-pending and commonly assigned U.S. patent application Ser. No. 09/993,988 filed Nov. 16, 2001 now U.S. Pat. No. 6,840,927.

FIELD OF THE INVENTION

This invention relates to an improved absorbent tampon with an overwrap or overwraps having both masking and wicking properties that provides enhanced leakage protection, and a clean post-use appearance.

BACKGROUND OF THE INVENTION

A wide variety of absorbent catamenial tampons have long been known in the art. While it has been found these tampons perform their intended function tolerably well, even the best of tampons do not always provide good coverage against leakage and possess a post-use appearance that has a negative impact on the consumer. Until recently it was not appreciated that post-use appearance of a tampon was an important factor affecting the consumer's total use experience and that consumers prefer tampons that maintain a clean post-use appearance. The design of overwraps or exterior surfaces of a tampon affects a tampon's comfort, as well as, the tampon's post-use appearance. Overwraps designed mainly with the comfort of the user in mind, reduce the adhesion to vaginal tissue by including hydrophobic materials and/or treatments in the design. It was found that the same hydrophobic materials that reduce adhesion and increase comfort might also be more pleasing to the user's perception of the tampon, post-use. These hydrophobic overwraps do not retain fluid and thus, yield a tampon with a clean post-use appearance.

While hydrophobic overwraps assist with the post-use appearance, they do not retain fluid, do not assist in the absorbing bypass fluid, or prevent bypass failure. Bypass failure occurs when the menses travels along the length of the vagina without contacting the tampon. During a tampon change, some residual menses may be left near the introitus of the vagina. This may be fluid which was previously absorbed, but which subsequently "squeezed out" of the tampon as it was withdrawn through the sphincter of the vagina. A replacement tampon may not effectively absorb the residual fluid, particularly if located near the introitus, i.e., in the lower vaginal cavity. Thus, in order to provide a solution a mechanism must be provided to absorb bypassed fluid from the lower vaginal cavity. One mechanism is to incorporate a wicking region or a wicking overwrap into the tampon of the present invention that covers at least a portion of the exterior surface of the absorbent member and extends beyond the withdrawal end to form a skirt portion.

Accordingly, it would be beneficial to have a tampon that, in addition to providing an improved appearance, can also provide a mechanism to absorb bypassed fluid from the lower vaginal cavity thereby increasing leakage protection.

BACKGROUND ART

U.S. Pat. No. 6,186,995 issued to John M. Tharpe on Feb. 13, 2001 relates to VAGINAL TAMPON AND METHOD FOR FABRICATION THEREOF.

SUMMARY OF THE INVENTION

This invention relates to catamenial tampons having a compressed absorbent member, and an overwrap comprising a masking region and a wicking region. The compressed absorbent member of the tampon has an inner region, an exterior surface, and an insertion end opposed to a withdrawal end. The overwrap comprises a masking region and a wicking region. The wicking region of the overwrap covers at least a portion of the exterior surface of the compressed absorbent member proximal to the withdrawal end of the compressed absorbent member. The masking region surrounds at least a portion of the exterior surface of the compressed absorbent member proximal to the insertion end of the compressed absorbent member.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
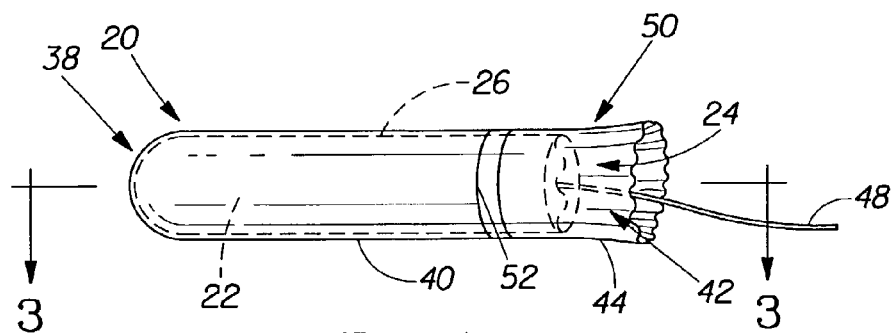
FIG. 1 is a perspective view of a tampon of the present invention incorporating a compressed absorbent member and an overwrap with a masking region and wicking region

As used herein "absorbent material" refers to a construction of the absorbent matter of a tampon without the overwrap material prior to the compression.

As used herein "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Thus as used herein, the term "compressed absorbent member" refers to the state of the absorbent material subsequent to compression. Conversely, the term "uncompressed" refers to the state of a material or materials prior to compression. In some embodiments, uncompressed tampons can be utilized in vivo. The term "compressible" is the ability of a material to undergo compression.

The term "folded" as used herein, is the configuration of the compressed absorbent member that may be incidental to lateral compression of the absorbent material or may purposely occur prior to a compression step. Such a configuration is readily recognizable, for example, when the absorbent material abruptly changes direction such that one part of the absorbent material bends and lies over another part of the absorbent material. When overwrap is placed on the absorbent material prior to compression, it too may be "folded."

As used herein "hydrophilic" and "hydrophobic" have meanings well established in the art with respect to the contact angle of a drop of water on the surface of a material. For example, a material having a contact angle of greater than about 75 degrees may be considered hydrophobic, and a material having a contact angle of less than about 75 degrees may be considered hydrophilic. Absolute values of hydrophobocity/hydrophilicity are not generally important, but relative values are. Thus, the absorbent member of the tampon and the wicking overwrap of the present invention are more hydrophilic than the masking overwrap, and the masking overwrap is more hydrophobic than the absorbent member and the wicking overwrap.

The term "joined" or "attached" as used herein, encompasses configurations in which a first element is directly secured to second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

As used herein "masking" or "fluid masking" refers to the property of a material to mask or make indistinct or imperceptible fluid, menstrual blood or menses that has been carried into the fibers of the absorbent material. As used "masking material" or "material that possess masking properties" are materials that have a critical surface tension of less than about 40 mN/m, preferably less than about 30 mN/m. "Masking materials" or "materials that possess masking properties" are materials, either wovens, nonowovens, or films, that may be comprised of a blend of natural fibers, synthetic fibers or natural and synthetic fibers that are hydrophobic or a combination of hydrophobic and hydrophilic fibers treated to be hydrophobic. The natural fibers include rayon, cotton, wood pulp, flax, and hemp. The synthetic fibers can include but are not limited to fibers such as polyester, polyolefin, nylon, polypropylene, polyethylene, polyacrylic, vinyl polyacetate, polyacrylate, cellulose acetate or bicomponent fibers. The treatments can include but are not limited to silicones, fatty acids (such as sucrose ester fatty acids), fluorocarbon, such as SCOTCHGUARD, and waxes. One embodiment of the masking overwrap comprises bicomponent fibers of polypropylene and polyethylene. Another embodiment of the masking overwrap comprises bicomponent fibers of polyester and polyethylene. One embodiment may include a nonwoven comprised of bicomponent fibers that have polypropylene core surrounded by polyethylene manufactured by Vliesstoffwerke Christian Heinrich Sandler GmbH & Co.KG (Schwarzenbach/Saale, Germany) under the tradename SAS B31812000. One embodiment may include a thermally bonded nonwoven of 17 g/m$^2$ basis weight manufactured by Vliesstoffwerke Christian Heinrich Sandler GmbH & Co.KG (Schwarzenbach/Saale, Germany) under the tradename Sawabond 4313.

The term "masking region" as used herein refers to the area of the overwrap that surrounds at least a portion of the compressed absorbent member proximal to the insertion end of the absorbent member.

As used herein "masking overwrap" refers to the material surrounding at least a portion of the exterior surface of the compressed absorbent member, the first surface and the second surface of the absorbent material, and/or the wicking overwrap. The masking overwrap may surround the exterior surface of the absorbent member and the first and second surface of the absorbent material as well as, any interior surfaces or interior regions due to the folding or rolling of the absorbent material during compression.

As used herein, the term "non-absorbent" refers to a structure that does not retain a significant portion of deposited fluid in its structure.

"Overlap" as used herein refers to the ordinary meaning of overlap. In all embodiments of the present invention "overlap" encompasses both partial and complete overlap.

The term "permeating" or "permeates" as used herein refers to the manner in which the masking overwrap and/or the wicking overwrap are positioned in relation to the inner region of the compressed absorbent member. As shown in the FIG. 6, the masking overwrap and/or the wicking overwrap extends from the exterior surface and follows the spiral (in the case of rolled) or serpentine (in the case of the folded) contours of the compressed absorbent member and thereby extends into the inner region of the member along the interstices formed by the contours of the rolls or folds. Any other compression methods are acceptable that result in the masking overwrap and/or the wicking overwrap similarly following the contours of the compressed absorbent member within the inner region. "Substantially permeating" and "substantially permeates" refer to when the masking overwrap and/or the wicking overwrap cover at least about 50% to about 100% of the surface area of the absorbent material, which after compression becomes the inner region of the compressed absorbent member.

The term "rolled" as used herein, is the configuration of the compressed absorbent member after winding the absorbent material and the overwrap or overwraps in a spiral round and round upon itself.

Unless specifically stated otherwise, as used herein a first material is "substantially covering" or "substantially covers" a second material when the first material covers at least about 50% to about 100% of the surface area of the second material.

The term "surrounds" as used herein refers to the manner in which a first material covers a second material when the first material covers the second material and/or when the first material covers a third material which covers the second material. In other words, a first material may "surround" a second material regardless of whether a third material or even a fourth material is interposed between the first material and the second material. For example, for the purposes of calculating the percentage of surface area of the exterior surface "surrounded by" the masking overwrap, one would disregard the presence of wicking overwrap falling between the masking overwrap surface and the exterior surface of the compressed absorbent material. Therefore, as used herein, a first material is "substantially surrounding" or "substantially surrounds" a second material when the first material covers from at least about 50% to about 100% of the surface area of the second material regardless of whether a third material is interposed between the first material and the second material. Thus, an embodiment where the wicking overwrap completely covers the exterior surface of the absorbent member and the masking overwrap covers 100% of the wicking overwrap would be described as a tampon having a masking overwrap "substantially surrounding" the exterior surface of the absorbent member. As well, an embodiment where the wicking overwrap completely covers the first surface and the second surface of the absorbent material and the masking overwrap covers 100% of the wicking overwrap would be described as a tampon having a masking overwrap "substantially surrounding" the first surface and the second surface of the absorbent material.

As used herein, "self-sustaining" is a measure of the degree or sufficiency to which the tampon retains the compression applied to the absorbent material such that in the subsequent absence of the external forces, the resulting tampon will tend to retain its general shape and size. For example, the resulting tampon's total volume growth subsequent to the removal of external forces may be no greater than about 50% of the external force-restrained shape, typically less than about 25% and preferably not to exceed about 10% of the external force-restrained shape when observed at ambient room conditions of 21–24° C. For tampons, it is found that control of the level of moisture within the tampon is a factor for helping the tampon to retain its shape subsequent the absence of the external compression forces. In one embodiment, the tampon is self-sustaining if the level of moisture is about 10% and not more than about 15%, of the basis weight. It will be understood by one of skill in the art that this self-sustaining form need not, and preferably does not persist during actual use of the tampon. That is, once the tampon is inserted and begins to acquire fluid, the tampon will begin to expand and may lose its self-sustaining form.

As used herein the term "tampon" refers to any type of absorbent structure that is inserted into the vaginal canal or other body cavities for the absorption of fluid therefrom, to aid in wound healing, or for the delivery of active materials, such as medicaments, or moisture. Tampons have a length, a width, a longitudinal axis and a radial axis. The tampon's length, can be measured from the insertion end to the withdrawal end along the longitudinal axis. A typical compressed tampon is 30–60 mm in length. A tampon may be straight or non-linear in shape, such as curved along the longitudinal axis. The width of a tampon, unless otherwise stated in the specification, corresponds to the largest cylindrical cross-section along the length. A typical compressed tampon is 8–20 mm wide. The tampon may be compressed into a generally cylindrical configuration in the radial direction, axially along the longitudinal and lateral axes or in both the radial and axial directions. While the tampon may be compressed into a substantially cylindrical configuration, other shapes are possible. These may include shapes having a cross section that may be described as rectangular, triangular, trapezoidal, semi-circular, hourglass, or other suitable shapes.

As used herein the terms "vaginal cavity," "within the vagina" and "vaginal interior," are intended to be synonymous and refer to the internal genitalia of the human female in the pudendal region of the body and does not include the interlabial space, including the floor of vestibule or the externally visible genitalia.

As used herein "wicking" refers to the ability of a material to transport liquid or moisture by capillary action. As used herein "wicking material" or "material that possess wicking properties" are materials that have the ability to wick deionized water to a height of 3 cm in less than 60 seconds when the nonwoven is disposed vertically over a reservoir of water. A method for quantifying such rate is provided in the Test Method section below. Such "wicking materials" or "materials that possess wicking properties" are materials, either wovens, nonowovens, or films, that may comprise a blend of natural fibers, synthetic fibers or natural and synthetic fibers. The wicking region and wicking overwrap are generally more hydrophilic than the absorbent material, absorbent member, the masking region and the masking overwrap. The natural fibers include rayon, cotton, wood pulp, flax, and hemp. Several embodiments of the wicking overwrap or wicking region include blends comprising from about 25% rayon to about 100% rayon. One embodiment includes a 100% rayon material. One embodiment may comprise 40 g/m$^2$ nonwoven comprising 100% rayon available as SX 275-123 produced by Green Bay Nonwovens, Green Bay, Wis. The synthetic fibers can include but are not limited to fibers such as polyester, polyolefin, nylon, polypropylene, polyethylene, polyacrylic, vinyl polyacetate, polyacrylate, cellulose acetate or bicomponent fibers. The blend of fibers forming the wicking overwrap can be made by any number of techniques. The blends may be carded on webs. Commonly, carded webs that are hydroentangled, thermally bonded, and resin bonded all have application. In the latter case, all natural fiber may be used with a significant portion of binder (10–30% is common). Spunbond and meltblown processes, combining synthetic fibers extruded/spun onto/into a mat or carded web of natural fibers provide other acceptable techniques. The basis weight of the material may fall into a range from about 10 to about 60 grams per square meter, or typically from about 15 to about 40 grams per square meter. In one embodiment, wicking material may comprise a hydroentangled blend of 50% rayon, 50% polyester available as BBA 140027 produced by BBA Corporation of South Carolina, U.S.A.

The term "wicking region" as used herein refers to the area of the overwrap that covers at least a portion of the compressed absorbent member proximal to the withdrawal end of the absorbent member.

As used herein "wicking overwrap" refers to the liquid pervious material covering at least a portion of the external surface of the compressed absorbent member proximal to withdrawal end of the absorbent member and/or, the first surface and the second surface of the absorbent material. The wicking overwrap optionally extends below the withdrawal end to define a skirt portion.

As used herein, "cm" is centimeter, "mL" is milliliters" "mm" is millimeters, "mN/m" is milliNewtons per meter, "g" is grams, "g/m$^2$" is grams per meter squared, and "s" is seconds.

While particular embodiments of the present invention have been illustrated and described, it would be obvious to those skilled in the art that various other changes and modifications can be made without departing from the spirit and scope of the invention.

1. Tampon of the Present Invention:

The tampon of the present invention comprises an overwrap or overwraps having masking and wicking properties. An embodiment of the tampon of the present invention with both a masking overwrap 40 and wicking overwrap 44 is shown in FIG. 1. The compressed absorbent member 22 has an exterior surface 26 and has an inner region 24 shown in greater detail below. The compressed absorbent member 22 has an insertion end 38 opposed to a withdrawal end 42. In FIG. 1, the fluid-masking overwrap 40 surrounds at least a portion of the exterior surface 26 of the compressed absorbent member 22. A wicking overwrap 44 covers at least a portion of the exterior surface 26 of the compressed absorbent member 22 proximal to the withdrawal end 42. In the embodiment shown in FIG. 1, the wicking overwrap 44 extends beyond over the withdrawal end 42 of the compressed absorbent member 22 to define a skirt portion 50. In this embodiment, the masking overwrap 40 and the wicking overwrap 44 overlaps at region 52. As well, this embodiment of the tampon 20 of the present invention includes a withdrawal means 48.

Figure 2:
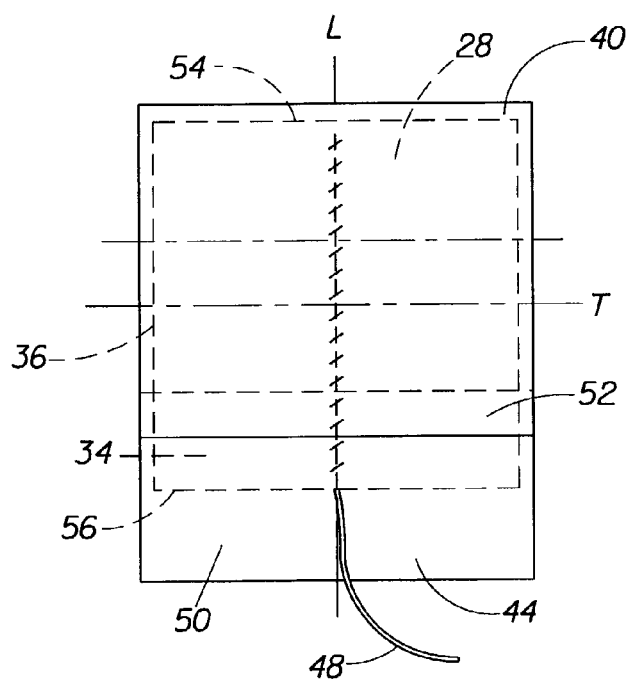
FIG. 2 is a perspective view of a tampon of the present invention incorporating a compressed absorbent and a masking overwrap, and a wicking overwrap defining a skirt.

FIG. 2 depicts a plan view of an uncompressed tampon including the absorbent material 28, masking overwrap 40 and wicking overwrap 44. The absorbent material 28 that has a first surface 34 opposed to the second surface 36 and an insertion end 54 opposed to a withdrawal end 56. The absorbent material 28 has both a longitudinal axis and a transverse axis indicated by the lines marked "L" and "T" respectively. The wicking overwrap 44 is positioned around the absorbent material 28 so that it covers at least a portion of the first surface 34 and second surface 36 proximal to the withdrawal end 56 of the absorbent material 28. In the embodiment shown in FIG. 2, the wicking overwrap 44 extends beyond the withdrawal end 56 of the absorbent material 28 the to define a skirt portion 50. The masking overwrap 40 surrounds at least a portion of the first surface 34 and opposed second surface 36 of the absorbent material 28. In the embodiment shown in FIG. 2, the masking overwrap 40 and the wicking overwrap 44 overlap at region 52. In one embodiment, the tampon 20 includes a withdrawal means 48. A tampon may be utilized in an uncompressed form. However, to form a compressed tampon, the absorbent material 28, the masking overwrap 40 and the wicking overwrap 44 are typically compressed and optionally heat conditioned in any suitable conventional manner known in the art.

Figure 3:
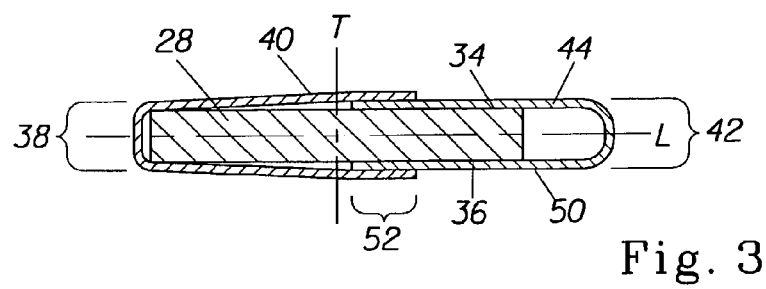
FIG. 3 is a plan view of an uncompressed tampon including the absorbent material, masking overwrap and wicking overwrap.

FIG. 3 shows a longitudinal cross section of an uncompressed tampon of the present invention comprising absorbent material 28, masking overwrap 40 and wicking overwrap 44 prior to compression. The absorbent material 28 has a first surface 34 opposed to the second surface 36. The absorbent material 28 is located in the center of the longitudinal cross-section. The masking overwrap 40 is positioned around a portion of the first surface 34 of the absorbent material 28 and the second surface 36 of the absorbent material 28. The wicking overwrap 44 is positioned around a portion of the first surface 34 of the absorbent material 28 and the second surface 36 proximal to the withdrawal end of the absorbent material 28. In the embodiment shown in FIG. 3, the masking overwrap 40 and the wicking overwrap 44 overlap at region 52.

Figure 4A:
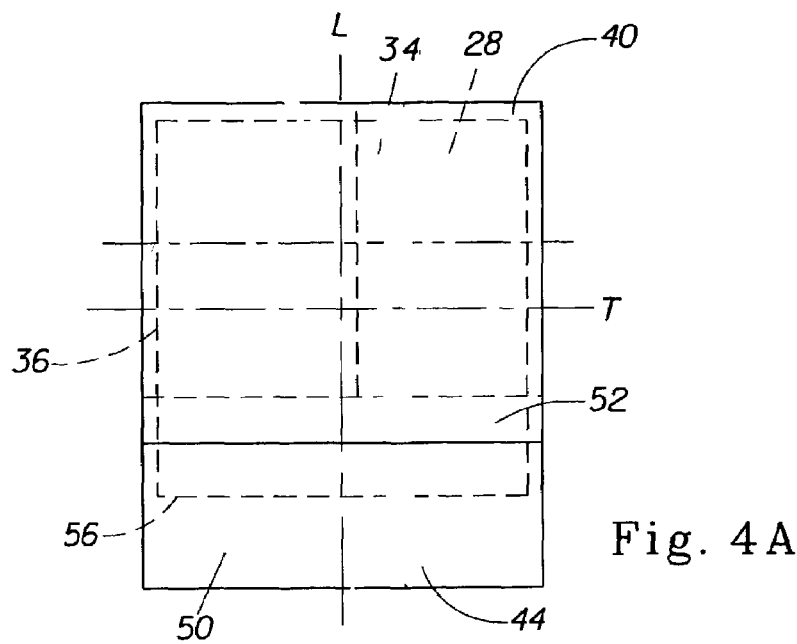
FIG. 4 is a longitudinal cross section of the absorbent material, masking overwrap, and wicking overwrap prior to compression.

FIG. 4A is a plan view of the absorbent material 28 with both the masking overwrap 40, and the wicking overwrap 44 wrapped transversely around the absorbent material 28. The wicking overwrap 44 is positioned around the first surface 34 and an opposed second surface 36 proximal to the withdrawal end 56 of the absorbent material 28 by wrapping around the transverse axis "T" of the absorbent material 28. In the embodiment shown in FIG. 4A, the wicking overwrap 44 extends beyond the withdrawal end 56 of the absorbent material 28 to define a skirt portion 50. In the embodiment shown, the masking overwrap 40 is tranversearound the first surface 34 and an opposed second surface 36 by wrapping around the longitudinal axis "T" of the absorbent material 28. The masking overwrap 40 and the wicking overwrap 44 overlap at region 52.

Figure 4B:
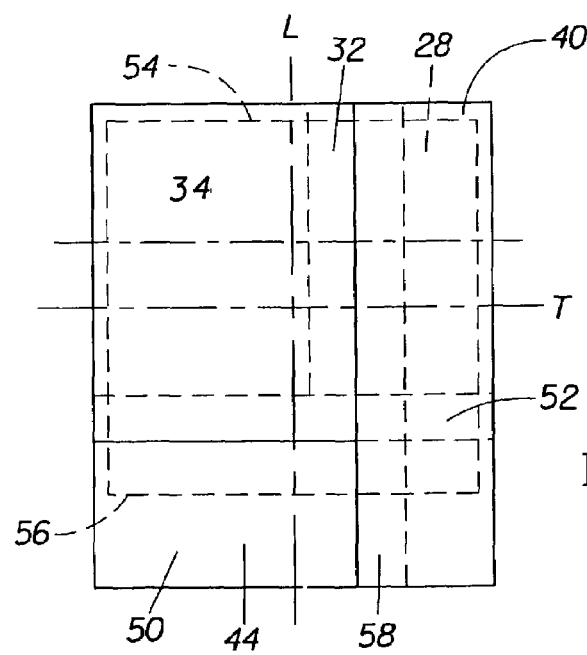

FIG. 4B is a plan view of the absorbent material 28 with the both the masking overwrap 40, and the wicking overwrap 44 wrapped longitudinally around the absorbent material 28. FIG. 4B shows an uncompressed tampon comprising an absorbent material 28, masking overwrap 40, and wicking overwrap 44. The wicking overwrap 44 is positioned around the first surface 34 and the second surface (not shown) proximal to the withdrawal end 42 by wrapping around the longitudinal axis "L" of the absorbent material 28. In the embodiment shown in FIG. 4B, the wicking overwrap 44 extends beyond the withdrawal end 56 of the absorbent material 28 to define a skirt portion 50. The wicking overwrap 44 overlaps with itself at region 58, as shown to the right of the longitudinal axis "L". The masking overwrap 40 is positioned around the first surface 34 and the second surface 36 by wrapping around the longitudinal axis "L" of the absorbent material 28. The masking overwrap 40 overlaps with itself at region 32, as shown to the right of the longitudinal axis "L". In the embodiment shown in FIG. 4B, the masking overwrap 40 and the wicking overwrap 44 overlap at region 52.

Figure 5A:
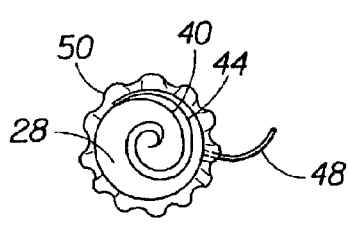
FIG. 5A is a plan view of the absorbent material with the masking overwrap and the wicking overwrap wrapped longitudinally around the absorbent material.

FIG. 5A shows an uncompressed tampon comprising the absorbent material 28, masking overwrap 40, and wicking overwrap 44. A skirt 50 and a withdrawal means 48 are also shown. FIG. 5A shows a cross-section of the compressed absorbent member. In the embodiment shown, the compressed absorbent member was constructed by surrounding at least a portion of the absorbent material 28 with the masking overwrap 40, covering at least a portion of the absorbent material 28 at the withdrawal end with a wicking overwrap 44. The absorbent material 28, masking overwrap 40, wicking overwrap 44 are rolled prior to compression. The resulting cross section taken proximal to the withdrawal end the tampon, therefore has a spiral of both the masking overwrap 40 and the wicking overwrap 44 within the inner region 24 of the compressed absorbent member 22. In the embodiment shown in FIG. 5A, the tampon has a skirt portion 50 withdrawal means 48.

Figure 5B:
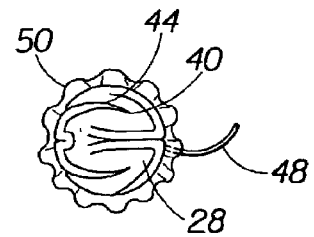
FIG. 5B is a plan view of the absorbent material, the masking overwrap, and the wicking overwrap wrapped transversely around the absorbent material.

FIG. 5B shows a cross-section of the compressed absorbent member. In the embodiment shown, the compressed absorbent member was constructed by surrounding at least a portion of the absorbent material 28 with the masking overwrap 40, covering at least a portion of the absorbent material 28 at the withdrawal end with a wicking overwrap 44. The absorbent material 28 masking overwrap 40, and wicking overwrap 44 are folded. The resulting cross section taken proximal to the withdrawal end the tampon, therefore, has a serpentine pattern of both the masking overwrap 40 and the wicking overwrap 44 within the inner region 24 of the compressed absorbent member. This serpentine pattern can take many shapes according to the folding process. In the embodiment shown in FIG. 5B, the tampon has a skirt portion 50 and withdrawal means 48.

Figure 6:
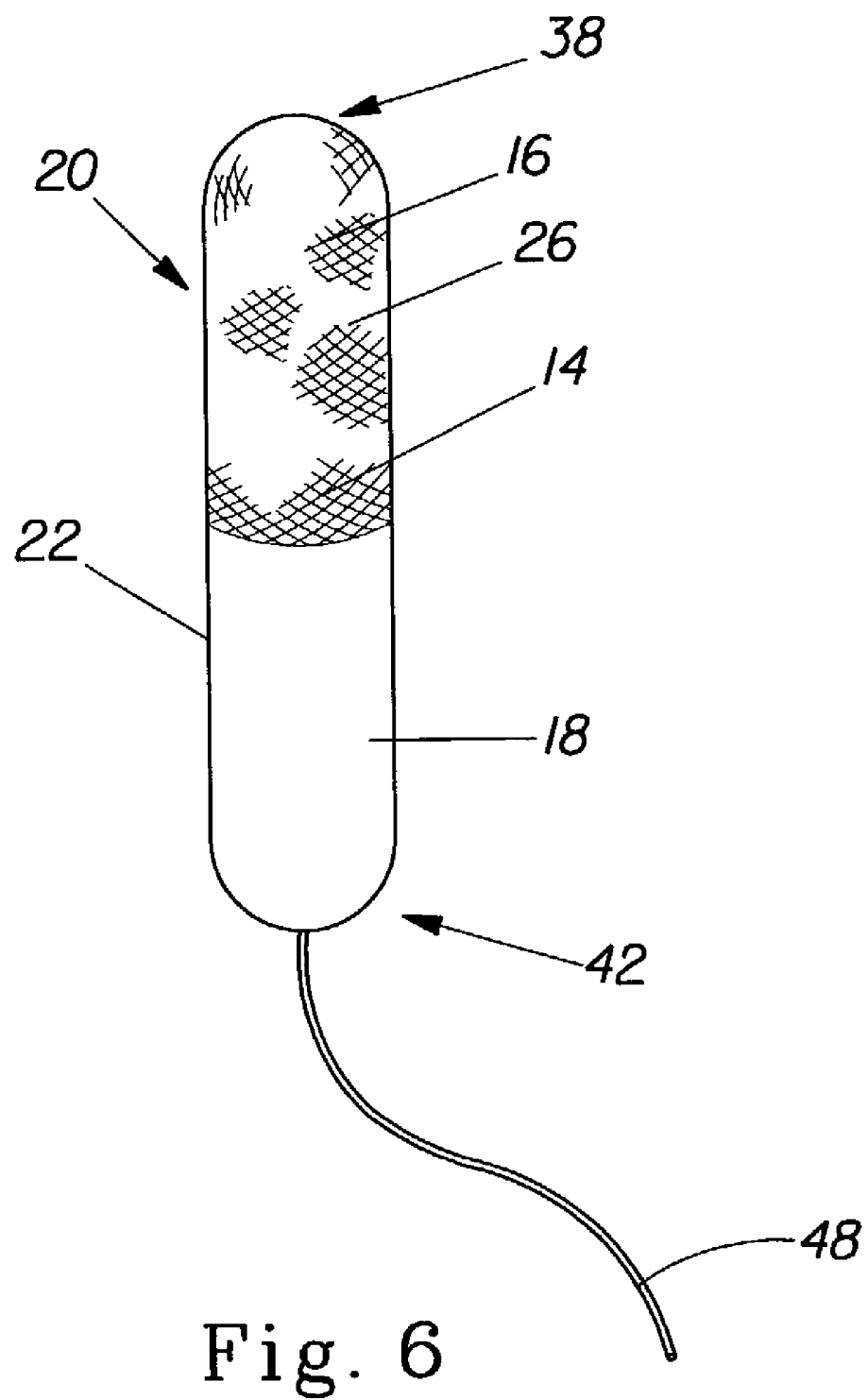
FIG. 6 is a plan view of the tampon of the present invention with masking and wicking properties in a single overwrap.

An embodiment of the tampon of the present invention with masking and wicking properties in a single overwrap is shown in FIG. 6. FIG. 6 shows the tampon 20 of the present invention comprising a compressed absorbent member 22 and an overwrap 14. The compressed absorbent member 22 of the tampon has an inner region, (not shown in FIG. 6) an exterior surface 26, and an insertion end 38 opposed to a withdrawal end 42. The overwrap 14 comprises a masking region 16 and a wicking region 18. The wicking region 18 of the overwrap covers at least a portion of the exterior surface 26 of the compressed absorbent member 22 proximal to the withdrawal end 42 of the compressed absorbent member 22. The masking region 16 surrounds at least a portion of the exterior surface 26 of the compressed absorbent member 22 proximal to the insertion end 38 of the compressed absorbent member 22.

a. Absorbent Material

The compressed absorbent member is comprised of absorbent material that has a first surface 34 opposed to the second surface 36 and an insertion end 54 opposed to a withdrawal end 56. The absorbent material has both a longitudinal axis and a transverse axis indicated by the lines marked "L" and "T" respectively. The absorbent material may be any suitable size and thickness suitable for compression into a tampon having a vaginally insertable shape. In the embodiment shown in FIG. 2, the absorbent material is generally square or rectangular, but other shapes such as trapezoidal, triangular, hemispherical, chevron and hourglass shaped are also acceptable. A typical size for absorbent material prior to compression may be from about 40 mm to about 100 mm in length and from about 40 mm to about 80 mm in width. The typical range for the overall basis weight is from about 150 g/m$^2$ to about 1000 g/m$^2$.

The absorbent material that comprises the compressed absorbent member may be constructed from a wide variety of liquid-absorbing materials commonly used in absorbent articles. Such materials include but are not limited to rayon (such as GALAXY Rayon (a tri-lobed rayon structure) available as 6140 Rayon; or SARILLE L rayon (a round fiber rayon), both available from Acordis Fibers Ltd., of Hollywall, England), cotton, folded tissues, woven materials, nonwoven webs, synthetic and/or natural fibers or sheeting, comminuted wood pulp which is generally referred to as airfelt, or combinations of these materials. Additional absorbent material include materials, such as peat moss, absorbent foams (such as those disclosed in U.S. Pat. No. 3,994,298 issued to DesMarais on Nov. 30, 1976, U.S. Pat. No. 5,795,921 issued to Dyer, et. al both incorporated by reference herein,) capillary channel fibers (such as those disclosed in U.S. Pat. No. 5,356,405 issued to Thompson, et. al incorporated by reference herein), high capacity fibers (such as those disclosed in U.S. Pat. No. 4,044,766 issued Kaczmarzk et al. Aug. 30, 1977 incorporated by reference herein), superabsorbent polymers or absorbent gelling materials (such as those disclosed in U.S. Pat. No. 5,830,543 issued to Miyake, et al incorporated by reference herein) may be incorporated into the tampon.

The absorbent material that comprises the compressed absorbent member can be rectangular or any other shape prior to compression and/or shaping. A more detailed description of liquid-absorbing materials shapes and dimensions can be found in co-pending case Ser. No. 10/039,979, filed Oct. 24, 2001, entitled "Improved Protection and Comfort Tampon", to Agyapong et al., Docket Number 8758.

b. The Overwrap Material

The tampon of the present invention comprises an overwrap or overwraps having masking and wicking properties. One embodiment of the tampon of the present invention comprises a tampon comprising an overwrap with both masking properties and wicking properties, made by treating portion of the overwrap to change the properties of te portion s described in the "The Process of Making" section below. Another embodiment of the tampon of the present invention comprises both a masking overwrap and a wicking overwrap. Unless otherwise noted in this section, "the overwrap material" refers to the overwrap with both masking properties and wicking properties, the masking overwrap and the wicking overwrap. In all embodiments shown, the overwrap material is generally rectangular, but other shapes such as trapezoidal, triangular, hemispherical, chevron, hourglass shaped, "T" and "L" shaped are also acceptable. Optimally, the overwrap material generally may both correspond to the shape of the absorbent material.

As discussed further in section entitled "Process of Making" the overwrap material may be wrapped in various configurations around the longitudinal axis "L" or the transverse axis "T". Because the overwrap material can be wrapped in the various configurations, the width and length of the overwrap material may vary. The width of the overwrap material may be wider or less wide than the measure of the longitudinal or transverse axis of the absorbent material it is being wrapped around. As well, the length of the overwrap may be longer or shorter than the measure of the longitudinal or transverse axis of the absorbent material it is being wrapped around.

In some embodiments, the overwrap material is wrapped in such a way that when the absorbent material and overwrap are compressed the overwrap may permeate at least a portion of the inner region of the absorbent member as discussed further in section entitled "Process of Making".

The overwrap material may be joined to the absorbent material by any variety of means. The overwrap materials may be joined to themselves, another overwrap, the compressed absorbent member or to the absorbent material. For example, one portion of wicking overwrap may be joined to an opposed portion of masking overwrap, wicking overwrap, the compressed absorbent member, or the absorbent material using any suitable adhesive or heat/pressure bonding means. Such bonding may extend continuously along the length of attachment or it may be applied in a "dotted" fashion at discrete intervals. Methods of bonding include thermally bonding, fusion bonding, or any other suitable means known in the art for joining such materials. Alternatively, the wicking overwrap may be joined to the absorbent material along with the withdrawal cord by stitching as shown in FIG. 3. Such stitching may use natural or synthetic thread.

A specific example of the tampon the folded compressed tampon of the present invention may comprises an absorbent material of 75% rayon and 25% cotton fiber with a basis weight of 600 g/m$^2$ having dimensions of 60 mm in width and 60 mm in length. The tampon may comprise a wicking overwrap of hydroentangled 50% rayon and 50% polyester fibers with a basis weight of 37 g/m$^2$ having dimensions of 110 mm in width and 60 mm in length. The wicking overwrap covers at least a portion of the first surface and second surface of the absorbent material. The wicking overwrap is wrapped around the longitudinal axis of the absorbent material such that 12 mm of the overwrap extends beyond the withdrawal end of the absorbent material. The tampon also comprises a masking overwrap of spunbound bicomponent with polyethylene and polypropylene fibers with a basis weigh of 17 g/m$^2$ having dimensions of 90 mm in width and 60 mm in length. The masking overwrap is surrounding at least a portion of the first surface and a second surface of the absorbent material and overlapping the wicking overwrap. The masking overwrap is wrapped around the longitudinal axis of the absorbent material. The absorbent material and overwrap are compressed axially and longitudinally then heated to form a compressed tampon of approximately 14 mm diameter and approximately 46 mm length.

c. Skirt Portion

In some embodiments, either the wicking region of the overwrap or the wicking overwrap may extend beyond the withdrawal end of the absorbent material and the compressed absorbent member to define a skirt portion. In some embodiments, the wicking region or the wicking overwrap may extend about 5 mm to about 40 mm, or even 2 mm to 25 mm beyond the withdrawal end defining a skirt portion. In other embodiments, the wicking region or the wicking overwrap may extend about 10 mm to about 15 mm beyond the withdrawal end defining a skirt portion. In one embodiment, the skirt portion may not be compressed. In all embodiments, the skirt is designed to draw bypassed fluid from the bottom of the vagina, thereby increasing absorbency and minimizing bypass discharge. Both the compressed absorbent member and skirt portion of the wicking overwrap may reside entirely within the vaginal cavity of the wearer during use of the tampon. This is achieved by the relative closeness of the skirt portion to the withdrawal end of the absorbent material as well of the relative size compared to the overall size of the tampon. In particular embodiments, only the withdrawal cord or other withdrawal means resides externally to the orifice of the vagina.

d. Optional Components

Some embodiments of the tampon of the present invention may comprise a withdrawal means. The withdrawal means could be joined to the tampon and graspable for digital removal after use. In one embodiment, the withdrawal means may be joined to at least the compressed absorbent member and extends beyond at least the withdrawal end of the compressed absorbent member. In another embodiment, the withdrawal means may be joined to at least the absorbent material and extends beyond at least the withdrawal end. Any of the withdrawal means currently known in the art may be used as a suitable withdrawal mechanism. In addition, the withdrawal means can take on other forms such as a ribbon, loop, tab, or the like. The withdrawal means may be integral with the absorbent material. Withdrawal cords useful in the present invention may be made of any suitable material known in the prior art and include cotton and polyester. Additionally, the tampons of the present invention may also benefit from a secondary absorbent member. U.S. Pat. No. 6,258,075 to Taylor et al. entitled "Tampon with Enhanced Leakage Protection" describes tampons having a variety of secondary absorbent members in great detail. The withdrawal means may be attached in any suitable manner known in the art including sewing, adhesive attachment, or a combination of known bonding methods. The withdrawal means may be joined to any suitable location on the tampon.

The tampon of the present invention may be inserted digitally or through the use of an applicator. Any of the currently available tampon applicators may also be used for insertion of the tampon of the present invention. Such applicators of typically a "tube and plunger" type arrangement and may be plastic, paper, or other suitable material. Additionally, a "compact" type applicator is also suitable.

II. Process of Making

While several methods of making the tampon of the present invention should be apparent to one of skill in the art in light of the disclosure herein, following is a description of some methods of making a tampon of the present invention.

The present invention relates to a tampon comprising an overwrap or overwraps with a masking and a wicking region. In some embodiments, one overwrap having a masking region and a wicking region are provided. In other embodiments two separate overwraps (a masking overwrap which becomes a masking region and a wicking overwrap which becomes wicking region) are provided to form the final overwrap (which may or may not be joined). Whether it is a masking region or a "separate" masking overwrap, the masking material may be hydrophobic or may be treated to render the region or overwrap hydrophobic if the starting if material is hydrophilic. Treatments that render a material hydrophobic include but are not limited to applying to or dipping the material in silicones, fatty acids (such as sucrose ester fatty esters), fluorocarbons, such as SCOTCHGUARD, and waxes. Whether it is a wicking region or a wicking overwrap, the wicking material may be hydrophilic or may treated to render the region or overwrap to be hydrophilic if the starting material is hydrophobic. Treatments that render a material hydrophilic include but are not limited to applying or dipping the material in surfactants, including non-ionic surfactants.

In other embodiments where two pieces of material are used to form the overwrap, a masking material/region/overwrap may be joined to a wicking material/region/overwrap by sewing, adhesives, bonding including thermally bonding, pressure fusion bonding, or any other suitable means known in the art for joining such materials. Alternatively, the two materials used to create the overwrap may not be physically connected at all.

In embodiments that begin with providing a compressed absorbent member, the compressed absorbent member has an exterior surface and an inner region and an insertion end opposed to a withdrawal end. The overwrap may be wrapped around a longitudinal axis or a transverse axis. The overwrap is positioned on the compressed absorbent member such that the wicking region/overwrap covers at least a portion of the exterior surface of the compressed absorbent member proximal to the withdrawal end and the masking region/overwrap surrounds at least a portion of the exterior surface of the compressed absorbent member proximal to the insertion end. In some embodiments, the wicking region/overwrap extends beyond the withdrawal end of the compressed absorbent member to define a skirt portion. In embodiments that begin with providing a compressed absorbent member, the overwrap, comprising both the wicking region/overwrap and the masking region/overwrap, may be joined or applied to the compressed absorbent member subsequent to compression. Alternatively, a wicking overwrap may be applied prior to compression (discussed further below) and a masking overwrap may be applied subsequent to compression. Overwraps applied subsequent to compression should be extensible such that the tampon will be able to expand within the vagina. The overwrap may be made extensible by processes such as, ring rolling, creping, MICREXing, and SELFing as described in U.S. Pat. No. 5,518,801 issued to Chappell on May 21, 1996, incorporated herein by reference.

Another approach to making tampons of the present invention involves wrapping the absorbent material (which is prior to compression). The absorbent material has a first surface opposed to the second surface and an insertion end opposed to a withdrawal end. The overwrap may be wrapped around a longitudinal axis or a transverse axis of the absorbent material. A wrapped absorbent is created by covering at least a portion of the first surface and second surface of the absorbent material with the wicking region/overwrap proximal to the withdrawal end of the absorbent material; and surrounding at least a portion of the first surface and the second surface of the absorbent material with the masking region/overwrap. In some embodiments, the wicking region/overwrap may extend beyond the withdrawal end of the absorbent material to define a skirt portion. In some embodiments, the wicking region/overwrap substantially covers the first surface and the second surface of the absorbent material such that the wicking overwrap is positioned between the exterior surface and the masking region/overwrap. As well, in some embodiments, the masking region/overwrap may substantially surround both the first surface and the second surface of the absorbent material.

The wrapped absorbent with a skirt is rolled or folded and/or compressed to form a compressed absorbent member having a vaginally insertable shape. Upon compression the masking overwrap surrounds at least a portion of the exterior surface of the compressed absorbent member and may permeate into the interstices of the inner region of the compressed absorbent member. Upon compression, the wicking overwrap covers at least a portion of the exterior surface of the tampon proximal to the withdrawal end and may permeate at least a portion of the inner region of the compressed absorbent member. In some embodiments, the masking overwrap and/or the wicking overwrap is positioned around the first surface and second surface such that when compressed, the masking overwrap and the wicking overwrap may substantially permeate the inner region of the compressed absorbent member subsequent to compression.

A hydrophilic nonwoven will typically wick the test fluid by at least about 3 cm in the initial 60 second period, preferably about 4 cm in the same period. A hydrophobic nonwoven will not wick fluid at all. A hydrophobic nonwoven may show a nonwetting meniscus at the point of contact with the fluid characteristic of a contact angle greater than 75°.

b. Critical Surface Tension

The critical surface tension of the hydrophobic nonwoven may be approximated by reducing the surface tension of the test liquid by addition of a surfactant to the point where the sample can wick the fluid to a height of about 5 cm in about 10 minutes according to the Wicking Rate Test above. The surface tension of the test fluid can at that point be measured by any suitable device (surface tensiometer). The surface tension approximates the critical surface tension of the nonwoven.

| Material | Time (s) | Average Distance Traveled by Test Fluid (mm) |
|---|---|---|
| An embodiment of the masking overwrap comprising a nonwoven comprised of bicomponent fibers under tradename SAS B31812000 manufactured by Vliesstoffwerke Christian Heinrich Sandler GmbH & Co. KG (Schwarzenbach/Saale, Germany) | 10 | 0 |
| | 20 | 0 |
| | 30 | 0 |
| | 40 | 0 |
| | 50 | 0 |
| | 60 | 0 |
| An embodiment of the wicking overwrap comprising a hydroentangled blend of 50% rayon, 50% polyester available as BBA 140027 produced by BBA Corporation of South Carolina, U.S.A. | 10 | 21 |
| | 20 | 28 |
| | 30 | 35 |
| | 40 | 39 |
| | 60 | 44 |
| An embodiment of the wicking overwrap comprising 40 g/m$^2$ nonwoven comprising 100% rayon available as SX 275–123 produced by Green Bay Nonwovens, Green Bay, WI. | 10 | 26 |
| | 20 | 38 |
| | 30 | 45 |
| | 40 | 50 |
| | 60 | 62 |

III. Test Methods a. Wicking Rate Test

This test measures how fast a nonwoven material wicks water against the force of gravity. The nonwoven sample is prepared by cutting an unwrinkled, smooth, straight-hanging piece having dimensions 2.5 cm in width and 20 cm in length. The sample is suspended vertically along the longest dimension using a clip or other attachment device that pinches only the uppermost 1 cm or less of the sample. A suitable distance measuring device such as a ruler is suspended adjacent to the sample not in direct contact with the sample. An open container of sufficient dimensions is used to hold 300 mL of test fluid. The test fluid is prepared by fully dissolving 0.20 g Indigo Carmine dye (other water soluble dyes which do not materially change the surface tension of the water may be used) in 1.00 L of water. The water used in this testing is deionized water having a surface tension of about 72 mN/m. The test is conducted under ambient conditions approximately 23° C. and 50%relative humidity. The container is elevated by means of a lab jack or other suitable device so as to make level contact with the bottom 0.5 cm of the hanging test nonwoven strip. Simultaneously with the contact, a timing device is started to measure elapsed time. The level of the wicking front of fluid is recorded for each 10 seconds for a period of at least about 120 seconds. This is the distance traveled per 10 second increment. The test is repeated with a fresh batch of test fluid for 2–3 replicates and the appropriately timed data points are averaged and plotted versus time as needed.

What is claimed is:

1. An uncompressed tampon comprising:
   an absorbent material having a first surface opposed to a second surface and an insertion end opposed to a withdrawal end;
   a wicking overwrap covering at least a portion of said first surface and said second surface proximal to said withdrawal end of said absorbent material;
   said wicking overwrap extending beyond the withdrawal end of said absorbent material to define a skirt portion;
   a masking overwrap surrounding at least a portion of said first surface and said second surface of said absorbent material;
   a withdrawal means attached to said absorbent material and extending beyond at least said withdrawal end.

2. An uncompressed tampon according to claim 1 wherein said masking overwrap substantially surrounds said first surface and said second surface of said absorbent material.

3. An uncompressed tampon according to claim 1 wherein said wicking overwrap substantially covers said first surface and said second surface of said absorbent material such that said wicking overwrap is positioned between the exterior surface and said masking overwrap.

4. An uncompressed tampon according to claim 1 wherein the masking overwrap comprises a nonwoven material comprising bicomponent fibers of polyproplene and polyethylene.

5. An uncompressed tampon according to claim 1 wherein the masking overwrap comprises a nonwoven material comprising bicomponent fibers of polyester and polyethylene.

6. An uncompressed tampon according to claim 1 wherein the wicking overwrap is 100% rayon.

7. An uncompressed tampon according to claim 1 wherein said wicking overwrap comprises a hydroentangled blend of 50% rayon and 50% polyester.

8. An uncompressed tampon according to claim 1 wherein said skirt portion extends from about 2 mm to about 25 mm from said withdrawal end of said absorbent material.

* * * * *